United States Patent [19]

Bell et al.

[11] Patent Number: 5,616,750

[45] Date of Patent: Apr. 1, 1997

[54] COMPOUNDS AND PROCESS

[75] Inventors: David Bell; David Miller; Robin P. Attrill, all of Harlow, England

[73] Assignee: SmithKline Beecham plc, United Kingdom

[21] Appl. No.: 129,162

[22] PCT Filed: Aug. 5, 1993

[86] PCT No.: PCT/GB93/01666

§ 371 Date: Oct. 6, 1993

§ 102(e) Date: Oct. 6, 1993

[87] PCT Pub. No.: WO94/03271

PCT Pub. Date: Feb. 17, 1994

[30] Foreign Application Priority Data

Aug. 6, 1992 [GB] United Kingdom ............ 9216662
Apr. 30, 1993 [GB] United Kingdom ............ 9308968

[51] Int. Cl.$^6$ .......... C07F 13/00; C07D 301/12; C07D 301/06

[52] U.S. Cl. .......... 556/32; 540/541; 544/4; 544/64; 544/225; 546/2; 548/101; 548/402; 549/3; 549/206; 549/531; 549/533; 556/45

[58] Field of Search .......... 556/45, 32; 549/531, 549/533, 3, 206; 548/101, 402; 546/2; 544/4, 64, 225; 540/541

[56] References Cited

U.S. PATENT DOCUMENTS 5,250,285 10/1993 Lauffer et al. .................. 424/9
5,420,314 5/1995 Katsuki et al. .................. 549/533

FOREIGN PATENT DOCUMENTS 0023075 1/1981 European Pat. Off. .
2588265 4/1987 France .
0090150 4/1989 Japan .
91/14694 10/1991 WIPO .

OTHER PUBLICATIONS

Journal of American Chemical Society, W. Zang, 'Enantioselective Epoxydation of Unfunctionalized Olefins Catalyzed By (Salen) Manganee Complex', vol. 112, Mar. 12, 1990, pp. 2801–2803.

Journal of American Chemical Society, K. Srinivasan, 'Epoxidation of Olefins With Cationic (Salen)MN Complexes.' vol. 108, 1986, pp. 2309–2320.

*Primary Examiner*—Porfirio Nazario-Gonzalez
*Attorney, Agent, or Firm*—James M. Kanagy; Stephen Venetianer; Edward T. Lentz

[57] ABSTRACT

A compound of formula (I):

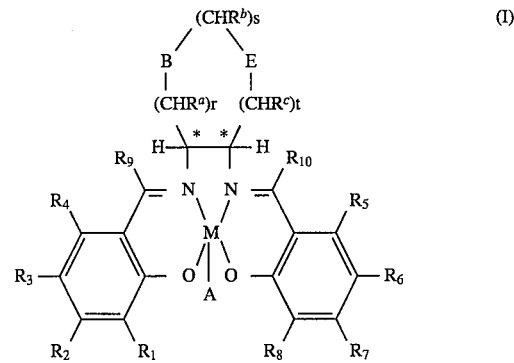

n which M is a transition metal ion;

A is a counter-ion if required;

r, s and t are independently 0 to 3 such that r+s+t is in the range of 1 to 3;

$R^a$, $R^b$, $R^c$ are each independently hydrogen or $CH_2OR'$ where R' is hydrogen or an organic group;

B and E are independently oxygen, $CH_2$, $NR^d$ in which $R^d$ is alkyl, hydrogen, alkylcarbonyl, or arylcarbonyl or $SO_n$ where n is 0 or an integer 1 or 2, with the proviso that B and E are not simultaneously $CH_2$ and that when B is oxygen, $NR^d$ or $SO_n$, then r cannot be 0, and when E is oxygen, $NR^d$ or $SO_n$, then t cannot be 0;

$R_1$, $R_2$, $R_3$, $R_4$, $R_5$, $R_6$, $R_7$, $R_8$, $R_9$ and $R_{10}$ are independently hydrogen, alkyl or alkoxy.

11 Claims, No Drawings

COMPOUNDS AND PROCESS

This application was filed under 35 U.S.S. §371 as a request for U.S. examination of International application No. PCT/GB93/01666, filed on Aug. 5, 1993.

This invention relates to novel catalysts and their use in the conversion of certain olefins into chirally enriched epoxides.

WO/91/14694 describes certain catalysts of the following formula (A):

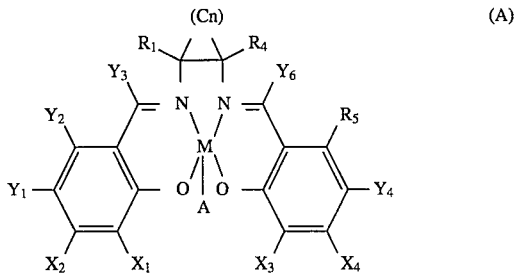

in which

M is a transition metal ion, A is an anion, and n is either 0, 1 or 2. At least one of $X_1$ or $X_2$ is selected from the group consisting or silyls, aryls, secondary alkyls and tertiary alkyls; and at least one of $X_3$ or $X_4$ is selected from the same group. $Y_1$, $Y_2$, $Y_3$, $Y_4$, $Y_5$ and $Y_6$ are independently selected from the group consisting of hydrogen, halides, alkyls, aryl groups, silyl groups, and alkyl groups bearing heteroatoms such as alkoxy and halide. Also, at least one of $R_1$, $R_2$, $R_3$ and $R_4$ is selected from a first group consisting of H, $CH_3$, $C_2H_5$ and primary alkyls. Furthermore, if $R_1$ is selected from said first group, then $R_2$ and $R_3$ arc selected from a second group consisting of alkyl groups, heteroatom-bearing aromatic groups, secondary alkyls and tertiary alkyls. If $R_2$ is selected from said first group, then $R_1$ and $R_4$ are selected from said second group. If $R_3$ is selected from said first group, then $R_1$ and $R_4$ are selected from said second group. If $R_4$ is selected from said first group, then $R_2$ and $R_3$ are selected from said second group.

Such catalysts are described as being useful in enantioselectively epoxidising a prochiral olefin.

Structurally distinct catalysts have now been prepared which surprisingly possess the ability to catalyse the enantioselective expoxidation of certain prochiral olefins.

Accordingly, the present invention provides a compound of formula (I):

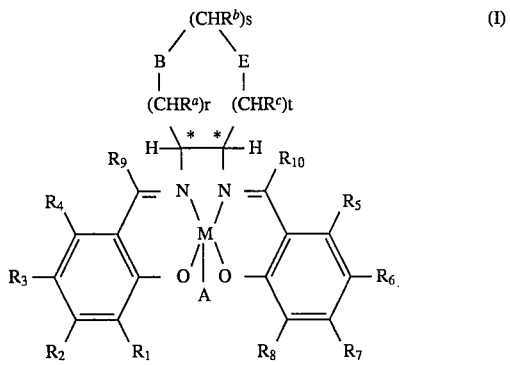

in which M is a transition metal ion;

A is a counter-ion if required;

r, s and t are independently 0 to 3 such that r+s+t is in the range of 1 to 3;

$R^a$, $R^b$, $R^c$ are each independently hydrogen or $CH_2OR'$ where R' is hydrogen or an organic group;

B and E are independently oxygen, $CH_2$, $NR^d$ in which $R^d$ is alkyl, hydrogen, alkylcarbonyl, or arylcarbonyl or $SO_n$ where n is 0 or an integer 1 or 2, with the proviso that B and E are not simultaneously $CH_2$ and that when B is oxygen, $NR^d$ or $SO_n$, then r cannot be 0, and when E is oxygen, $NR^d$ or $SO_n$, then t cannot be 0;

$R_1$, $R_2$, $R_3$, $R_4$, $R_5$, $R_6$, $R_7$, $R_8$, $R_9$ and $R_{10}$ are independently hydrogen, alkyl or alkoxy.

Suitable transition metal ions, M, include Mn, Cr, Fe, Ni, Co, Ti, V, Ru and Os in an appropriate oxidation state.

Preferably the transition metal ion, M, is Mn in oxidation state (II) or (III).

It should be appreciated that in some cases for example when M is Mn (II), a counter-ion is not required.

Suitable counter-ions, A, include those anions mentioned in WO 91/14694.

Preferably, A is chloride.

Suitable organic groups R' include alkyl, alkylcarbonyl, arylcarbonyl or aryl derivatives.

Particular examples of R' include substituted alkyl groups.

One example of R' is triphenylmethyl.

Preferably s and t are zero, r is 1 and $R^a$ is hydrogen, B is oxygen and E is $CH_2$; or r, s and t are 1, $R^a$, $R^b$ and $R^c$ are hydrogen and B and E are both oxygen; or s is zero, r and t are both 1, $R^a$ is hydrogen or triphenylmethyloxymethylene and $R^c$ is hydrogen, B is oxygen and E is —$CH_2$—; or r and t are both 1, s is zero, $R^a$ and $R^c$ are hydrogen, B is $NR^d$ where $R^d$ is phenyl carbonyl and E is $CH_2$.

Suitably, $R_2$, $R_4$, $R_5$ and $R_7$ each independently represent hydrogen.

Suitably $R_1$, $R_3$, $R_6$ and $R_8$ each independently represent C 1-6 alkyl.

Favourably $R_1$ and $R_8$ represent branched alkyl groups such as tertiary alkyl groups.

$R_3$ and $R_6$ also advantageously represent branched alkyl groups.

One preferred example for each of $R_1$ and $R_8$ is tertiary butyl.

Particular examples of $R_3$ and $R_6$ are tertiary butyl and methyl.

Examples of $R_2$, $R_4$, $R_5$ and $R_7$ are hydrogen.

The term 'alkyl' when used alone or when forming pan of other groups (for example alkoxy groups or alkycarbonyl groups) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

When used herein the term 'aryl' includes phenyl and naphthyl optionally substituted with up to five, preferably up to three, groups selected from halogen, alkyl, phenyl, alkoxy, haloalkyl, alkylcarbonyl and phenylcarbonyl.

A preferred aryl group is a substituted or unsubstituted phenyl group.

Transition metals M include those having oxidation states of (II) or more.

Suitable substituents for aryl include alkyl, halogen and alkoxy.

Optional substituents for alkyl groups include those mentioned herein for aryl groups, phenyl is a particular example.

It should be appreciated that the carbon atoms marked with an asterisk are chiral centres and the present invention extends to each individual enantiomer and any mixtures thereof.

The present invention also provides a process for the preparation of compounds of formula (I) which comprises forming a transition metal complex of the following compound of formula (II):

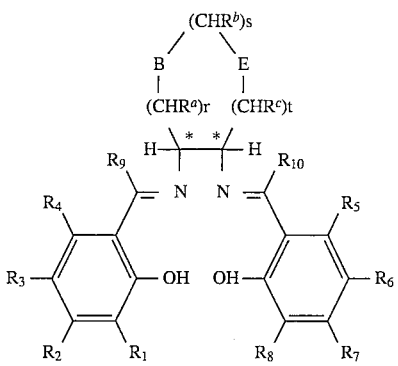

where variables $R_1$ to $R_{10}$, B, E, r, s, t $R^a$, $R^b$ and $R^c$ are as defined in relation to formula (I), and thereafter if necessary separating any enantiomers.

Suitably the transition metal ion complex may be formed by the addition of a suitable transition metal salt such as manganese (II) or (III) acetate, preferably manganese (III) acetate, to a compound of formula (II) in a suitable solvent such as ethanol or methylene dichloride, at elevated temperature. The optional replacement or interconversion of the counter ion may be effected by the addition of an alkali metal salt containing the desired counter-ion such as LiCl.

The separation of any enantiomers may be carried out by conventional techniques, such as crystallisation of derivatives or chromatography. However, it should be appreciated that is is preferred that separation of enantiomers is carried out before forming a transition metal complex.

The invention further provides a process for the preparation of compounds of formula (II) which comprises condensing sequentially, in any order, a compound of formula (III):

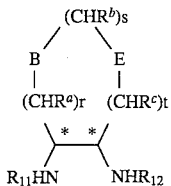

where r, s, t, $R^a$, $R^b$ and $R^c$ E, B are as defined in formula (I) and $R_{11}$ and $R_{12}$ independently represent hydrogen or an amine protecting group, providing at least one of $R_{11}$ and R12 is hydrogen, with a compound of formula (IV);

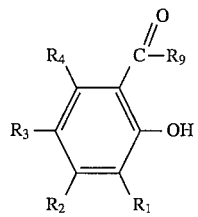

and a compound of formula (V), removing any protecting group $R_{11}$ or $R_{12}$ as necessary;

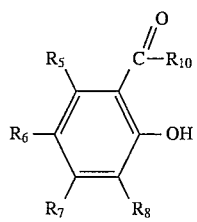

wherein $R_1$ to $R_{10}$ are as defined in relation to formula (I), and thereafter as required isolating the required compound including if necessary separating any enantiomers.

It is preferred that the compound of formula (II) is prepared from optically pure compounds of formula (III) which are preferably prepared themselves from optically pure starting materials. Alternatively, racemates or mixtures of enantiomers of formula (II) or (III) may themselves be resolved using conventional techniques in the art such as crystallisation of derivatives, or chromatography.

When compounds of formula (II) are required in which one or more of $R_1$, $R_2$, $R_3$, $R_4$ and $R_9$ are not the same as one or more of $R_8$, $R_7$, $R_6$, $R_5$ and $R_{10}$ respectively, then compounds of formula (III) may be sequentially condensed with compounds of formula (IV) and formula (V), in any order, by heating a suitably protected compound of formula (III) with a compound of formula (IV) or (V) (in a 1:1 mole ratio) in an inert solvent such as ethanol, if necessary, purifying the resulting intermediate compound of formula (VI) or (VII):

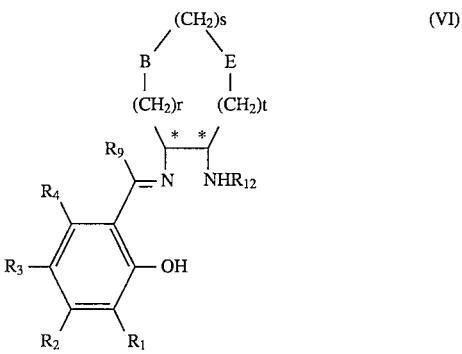

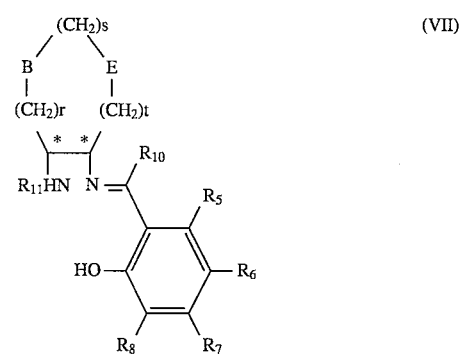

wherein variables $R_1$ to $R_{12}$, r, s, t, $R^a$, $R^b$, $R^c$, E and B are as defined in to formula (III), (IV) and (V) using conventional techniques such as chromatography removing any $R_{11}$ or $R_{12}$ protecting groups and then repeating the reaction using a compound of formula (IV) or (V) as required.

Suitable protecting groups $R_{11}$ or $R_{12}$ include conventional amine protecting groups such as benzyl groups, silyl groups or acyl groups such as benzoyl groups.

The removal of $R_{11}$ or $R_{12}$ when representing protecting groups may be carried out using conventional techniques in the art depending upon the nature of the protecting group.

It should be appreciated that when each of $R_1$, $R_2$, $R_3$, $R_4$ and $R_9$ is the same as each of $R_8$, $R_7$, $R_6$, $R_5$ and $R_{10}$ respectively the compounds of formula (IV) and (V) are the same, therefore, compounds of formula (III) in which $R_{11}$ and $R_{12}$ is hydrogen are preferably used and two moles of a compound of formula (IV) or (V) are utilised, in an inert solvent, such as ethanol, at elevated temperature, for example at reflux.

Compounds of formula (III) are either known compounds or may be prepared according to known methods or analogously to known methods or analogously to the methods described herein, for example when a compound of formula (III) is: 3,4-diaminotetrahydrofuran, such a compound may be prepared according to the following scheme, for example, as described in descriptions 1 and 2.

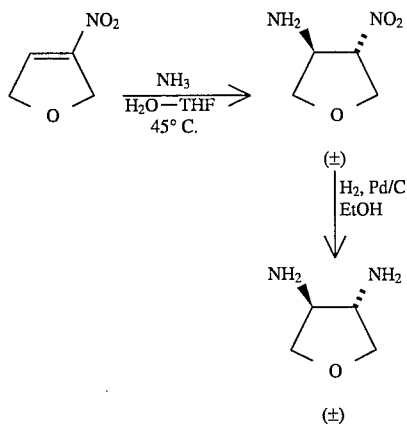

Alternatively, 3,4-diaminotetrahydrofuran may be prepared according to the following scheme, for example, as described in descriptions 4 to 6.

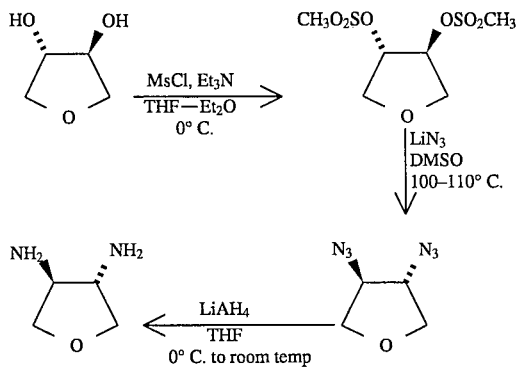

The 5R, 6R-diamino-1,3-dioxepane may be prepared according to the procedures, as described in descriptions 8 to 13.

The 3R, 4S-diamino tetrahydropyran may be prepared according to the procedures as described in descriptions 15 to 17.

The 3R,4R-diamino-(2R)(triphenyl methoxymethyl)tetrahydrofuran may be prepared according to the procedures as described in descriptions 21 to 24.

The (±) trans-1-benzoyl-3,4-diaminopiperidine may be prepared according to the procedures as described in descriptions 25 to 27.

Compounds of formula (IV) and (V) are either commercially available, are known compounds or may be prepared according to known methods or analogously to known methods for examples such as these described by G. Casiraghi et al J. Chem Soc. Perkin Transactions I. 1980 P 1862–1865.

Novel compounds of formula (II), (III), (IV), (V), (VI) and (VII) form an aspect of the present invention.

It should be appreciated that the term chiral catalyst refers to catalysts of formula (I) which have a predominance of one particular enantiomer and therefore are useful in forming a predominance of one particular enantiomer of the resulting epoxide produced from a prochiral olefin.

It should be appreciated that the catalysts, of formula (I) are preferably prepared in a chiral form by using a resolved compound of formula (III) which may be resolved using conventional techniques. The compound of formula (III) may itself be prepared from suitable precusor compounds such as these outlined in hereinbefore which may be resolved using conventional techniques or may be purchased in a resolved form. Alternatively, the coupled compound of formula (II) may be resolved using conventional techniques.

The invention further provides a process for enantioselectively epoxidising a prochiral olefin in the presence of an oxygen source and a chiral catalyst of formula (I).

Suitable prochiral olefins include compounds which comprise the following groups as part of their structure, cyclohexene, 5,6-dihydro-2H-pyran, 1,2,5,6-tetrahydropyridine, 1,2,3,4-tetrahydropyridine and 5,6-dihydro-2H-thiopyran.

Favoured prochiral olefins include those compounds which comprise the following groups as part of their structure form: 1,2-dihydronaphthalene, 2H-chromene, 1,2-dihydroquinoline, 1,2-dihydroisoquinoline and 2H-thiochromene.

Such compounds are well known in the potassium channel activator field.

Preferably, prochiral olefins include those mentioned in EP-A-0 376 524, such as the compounds of formula (XIV) therein, and in particular 2,2-dimethyl-6-pentafluoroethyl-2H- 1-benzopyran.

It should be appreciated that the present invention particularly extends to the preparation of all epoxide precursors to those compounds of formula (I) in EP-A-0 376 524 and especially the specific examples thereof using the herein described process.

The present invention also particularly extends to the subsequent conversion of all epoxide precursors to all specific examples in EP-A-0 376 524, to those specific examples in particular to the preparation of (−)trans-3,4-dihydro-2,2-dimethyl-4-(2-oxopiperidin- 1-yl) 6-pentafluoroethyl-2H-1-benzopyran-3-ol.

Suitable oxygen sources include sodium hypochlorite.

It should be appreciated that only one enantiomer of a catalyst of formula (I) is required to produce the 3S,4S enantiomer of the epoxide precursor to compounds described in EP-A-0 376 524 which in turn produce the 3S,4R configuration in the compounds of formula (I) as described in EP-A-0 376 524. Conversely, the 3R, 4R enantiomers of the epoxide precursors produce the 3R, 4S configuration in the compounds of formula (I) as described in EP-A-0376 524.

The following descriptions and examples illustrate the present invention.

DESCRIPTION 1

(±) 2,5-Dihydro-3-nitrofuran (D1)

A mixture of (±) trans 3-chloromercurio-4-nitro-2,5-dihydrofuran[1] (38.54 g, 109.6 mmol) and Et$_3$N (11.07 g, 109.6 mmol) in CH$_2$Cl$_2$ (2.2 L) at 25° C. was stirred for 1.25 h. 5% aqueous citric acid (1.1 L) was added and stirring was continued for 5 min. The mixture was filtered through celite, separated and the organic phase washed with 5% aqueous citric acid (220 ml), dried over Na$_2$SO$_4$ and concentrated in vacuo. Chromatography of the residue on silica (Merck 9385, 300 g) eluting with CHCl$_3$-Hexane (1:1>1:0) afforded (D1) as a pale yellow oil which crystallised in the freezer, 5.45 g (43.2%).

δ (CDCl$_3$) 4.95 (4H,S) and 7.10 (1H, S)

1. P. Bitha and Y—I. Lin, J. Heterocyclic Chem., 1988, 25, 1035–1036.

DESCRIPTION 2

(±) 3,4-Diaminotetrahydrofuran (D2)

A solution of (±) 4-amino-3-nitrotetrahydrofuran, prepared from (D1) via the method of Bitha and Lin[1], (4.66 g, 35.3 mmol) in EtOH (100 ml) containing 10% palladium on carbon (2.5 g) was hydrogenated on a Parr shaker apparatus at 35 psi for 65 h at 20° C. The suspension was filtered, the solids washed with EtOH (100 ml) and the combined filtrate evaporated in vacuo to afford (±) (D2) as a colourless oil, 3.26 g (81.5%)

δ (CDCl$_3$) 1.40 (4H,bs), 3.20 (2H, m), 3.50 (2H,dd) and 4.08 (2H,dd).

DESCRIPTION 3

(±) 3,4-bis (3-tert-Butyl-5-methylsalicylideamino)tetrahydrofuran (D3)

A solution of the racemic diamine (D2) (855 mg, 8.38 mmol) and 3-tert-butyl-5-methylsalicaldehyde (3.22 g 16.76 mmol) in EtOH (50 ml) was heated at reflux for 1.5 h. The solvent was removed in vacuo and the residue chromatographed on silica (Merck 9385, 300 g) using CHCl$_3$ as eluent to afford (±) (D3) as pale yellow needles, 1.35 g, (35.8%).

δ (CDCl$_3$) 1.42 (18H,s), 2.25 (6H,s), 3.95–4.10 (2H,m), 4.43 (2H,q), 6.90 (2H,d), 7.15 (2H,d), 8.30 (2H,s) and 13.10 (2H,bs).

DESCRIPTION 4

(S,S) trans 3,4-bis(methanesulphonyloxy)tetrahydrofuran (D4)

A solution of 1,4-anhydro-L-threitol (2.45 g, 23.5 mmol ex Aldrich Chemical company) in a mixture of THF (75 ml) and Et$_2$O (75 ml) at 0° C. was treated sequentially with triethylamine (7.2 ml, 51.7 mmol, 2.2 eq) and methanesulphonyl chloride (3.82 ml, 49.35 mmol, 2.1 eq). The mixture was stirred for 4h then stored at 0° C. overnight (~16 h).

The reaction was filtered and the solids washed with THF (20 ml). The combined filtrate was evaporated in vacuo and partitioned between 10% aqueous citric acid (60 ml) and EtOAc (150 ml). The organic phase was dried (MgSO$_4$) and evaporated to afford (D4) as a colourless oil, 5.82 g (95%).

δ (CDCl$_3$) 3.12 (6H,s) 4.00 (2H,dd), 4.18 (2H,dd) and 5.25 (2H,dd).

DESCRIPTION 5

(S,S) trans 3,4-Diazidotetrahydrofuran (DS)

A mixture of the dimesylate (D4) (5.80 g, 22.3 mmol) and lithium azide (5.46, 111.5 mmol, 2.5 eq) in DMSO (60 ml) was heated at 100°–110° C. for 40 h. After cooling to ambient the reaction was diluted with water (IL) and extracted with EtOAc (IL, 2×0.75 L). The combined organic phase was washed with water (0.5 L) and brine (0.5 L), dried over MgSO$_4$ and evaporated in vacuo to a pale yellow oil of the title compound, 2.18 g (61.5%).

δ (CDCl$_3$) 3.75 (2H,dd) and 3.90–4.05 (4H,m).

DESCRIPTION 6

(S,S) trans 3,4-Diaminotetrahydrofuran

To lithium aluminium hydride (2.05 g, 54 mmol) in dry THF (150 ml) at 0° C. was added the diazide (D5) (2.08 g, 13.5 mmol) in THF (50 ml) dropwise over 10 min. After 15 min the solution was allowed to warm to ambient, then stirred for 16 h.

The reaction mixture was re-cooled to 0° C. and quenched sequentially with H$_2$O (2 ml), 15% aqueous NaOH (2 ml) and further H$_2$O (6 ml) and warmed to ambient. After stirring for 1 h the mixture was filtered through celite, rinsed with THF (2×150 ml) and the combined filtrate evaporated in vacuo to afford (D6) as a pale yellow oil, 1.28 g (93%).

δ (CDCl$_3$) 1.30 (4H,bs), 3.20 (2H,dd), 3.50 (2H,dd) and 4.08 (2H,dd).

DESCRIPTION 7

(S,S) trans 3,4-bis(3-tert-Butyl-5-methylsalicylideamino)tetrahydrofuran (D7)

A solution of the (S,S)-diamine (D6) (1.26 g, 12.35 mmol) and 3-tert-butyl-5-methylsalicaldehyde (4.74 g, 24.70 mmol) in EtOH (75 ml) was heated at reflux for 3.5 h. The solution was cooled and solvent removed in vacuo to afford crude (5) as a yellow oil, 5.50 g (99%).

A sample of the crude material (4.55 g) was chromatographed on silica (Merck 9385, gradient of CHCl$_3$ in hexane) to afford pure (D7) as a yellow foam, 4.39 g (95.5% yield).

δ(CDCl$_3$) 1.42 (18H,s), 2.25 (6H,s), 3.95–4.10 (4H,m) 4.33 (2H,q), 6.90 (2H,d), 7.15 (2H,d), 8.30 (2H,s) and 13.15 (2H,bs).

DESCRIPTION 8

(2R,3R)-1,4-Dibenzyloxy-2,3-dimethanesultionyloxybutane

To a solution of (2R,3R)-(+)-1,4-dibenzyloxy-2,3-butanediol (25.3 g, 83.7 mmol ex Aldrich Chemical Company) in dichloromethane (165 ml), cooled in an ice bath, was added methanesultionyl chloride (13.0 ml, 167.4 mmol), followed by slow addition of triethylamine (23.3 ml, 167.4 mmol) such that the temperature did not rise above 5° C. Once the addition was complete the reaction was allowed to stir with ice-bath cooling for 3 hours. Water (600 ml) was then added and the organic phase separated. The aqueous phase was re-extracted with dichloromethane (200 ml) and the combined organic phases washed with water (400 ml) and brine (400 ml), dried (MgSO$_4$), and the solvent evaporated to afford a pale yellow solid. Trituration with diethyl ether afforded the title compound (28.2 g, 74%) as colourless crystals m.p. 72°–73° C.

$^1$H n.m.r. (CDCl$_3$):δ3.03 (s,6H,2×CH$_3$), 3.76 (m,4H,2×CH$_2$O), 4.48 (d,2H,CH$_2$Ph), 4.57 (d,2H,CH$_2$Ph), 5.00 (m,2H,2×CH), 7.27–7.39 (m,10H,2×Ph)

$^{13}$C n.m.r. (CDCl$_3$):δ38.8 (2×CH$_3$), 68.7 (2×CH$_2$) 73.7 (2×CH$_2$), 78.7 (2×CH), 128.1, 128.2, 128.6, 137.0 (2×Ph).

EI-MS:m/e 459 (MH$^+$), 367 (M$^+$-CH$_2$Ph).

C$_{20}$H$_{26}$O$_8$S$_2$ requires: C: 52.39, H:5.72% found: C: 52.36, H:5.59%.

DESCRIPTION 9

(2R,3R)-Dimethanesultionyloxybutane-1,4-diol (2R,3R)-1,4-Dibenzyloxy-2,3-dimethanesultionyloxybutane (27.6 g, 60.3 mmol) (D8) was dissolved in acetone (500 ml), a suspension of 10% Pd/C (29.9 g) in acetone (300 ml) added, and the mixture hydrogenated at 1 atm. pressure for 2 hours at ambient temperature. The mixture was then filtered three times through a pad of silica and Celite, and the solvent evaporated to give the title compound as a straw-coloured oil (14.7 g, 87%), which solidified on standing.

$^1$H n.m.r. (DMSO-$d_6$): δ3.24 (s,6H, 2×CH$_3$), 3.69 (m,4H, 2×CH$_2$), 476 (m,2H,2×CH), 5.33 (t,2H,2×OH).

$^{13}$C n.m.r. (DMSO-$d_6$): δ38.1 (2×CH$_3$), 59.7 (2×CH$_2$), 80.3 (2×CH).

EI-MS:m/e 279 (MH$^+$), 261 (MH$^+$-H$_2$O), 183 (M$^+$-OMs), 165 (M$^+$-OMs,H$_2$O).

DESCRIPTION 10

(6R,7R)-Dimethanesultionyloxy-2,4,9,11-tetraoxadodecane (2R,3R)-Dimethanesultionyloxybutane-1,4-diol (14.7 g, 52.9 mmol) (D9) was dissolved in dimethoxymethane (89.5 ml) and dichloromethane (30 ml) at 40° C. Lithium bromide (0.91 g) and p-toluenesultionic acid monohydrate (1.01 g, 5.29 mmol) were added, and the mixture heated under reflux for 3 hours. The reaction was allowed to cool to ambient temperature, and then poured into saturated sodium bicarbonate solution (200 ml), extracted with ethyl acetate (2×200 ml), dried (MgSO$_4$) and evaporated to give a colourless oil. This was purified by column chromatography on silica, eluting with 0–1% methanol in dichloromethane, to afford the title compound as a colourless oil (8.2 g, 42%).

$^1$H n.m.r. (CDCl$_3$): δ3.13 (s,6H,2×CH$_3$), 3.39 (s,6H,2×OCH$_3$), 3.87 (m,4H,2×CH$_2$), 4.66 (m,4H,2×OCH$_2$O), 5.02 (m,2H,2×CH).

$^{13}$C n.m.r. (CDCl$_3$): δ38.8 (2×SCH$_3$), 55.8 (2×OCH$_3$), 66.1 (2×CH$_2$), 78.4 (2×CH), 96.8 (2×OCH$_2$O)

CI-MS:m/e 384 (MNH$_4^+$).

C$_{10}$H$_{22}$O$_{10}$S$_2$ requires: C: 32.78, H: 6.05% found: C: 32.22, H: 5.62%.

DESCRIPTION 11

(5R,6R)-Dimethanesultionyloxy-1,3-dioxepane

A solution of (6R,7R)-dimethanesultionyloxy-2,4,9,11-tetraoxadodecane (8.2 g, 22.4 mmol) (D10) and p-toluenesultionic acid monohydrate (0.26 g, 1.34 mmol) in toluene (165 ml) was heated under reflux overnight. The solvent was evaporated and the brown residue triturated with diethyl ether to afford the title compound as an off-white solid (5.9 g, 91%) m.p. 133°–134° C.

$^1$H n.m.r. (CDCl$_3$): δ3.13 (s,6H,2×CH$_3$), 3.84 (m,2H, CH$_2$), 4.06 (m,2H,CH$_2$), (m,2H,CH$_2$), 4.77 (s,2H, OCH$_2$O), 4.81 (m,2H,2×CH).

$^{13}$C n.m.r. (CDCl$_3$): δ38.8 (2×CH$_3$), 64.1 (2×CH$_2$) 78.3 (2×CH), 94.6 (OCH$_2$O).

EI-MS:m/e 291 (MNH$^+$).195 (M$^+$-OMs).

C$_7$H$_{14}$O$_8$S$_2$ requires: C: 28.96, H: 4.86% found: C: 29.22, H: 4.61%. DESCRIPTION 12

(5R,6R)-Diazido-1,3-dioxepane

A mixture of (5R,6R)-dimethanesultionyloxy-1,3-dioxepane (5.0 g, 17.2 mmol) D11 and lithium azide (4.2 g, 86 mmol) in dimethylsulphoxide (60 ml) was stirred and heated to 110°–120° C. overnight. The reaction mixture was then cooled, poured into water (200 ml), and extracted with ethyl acetate (2×150 ml). The combined organic phases were washed with water (2×150 ml) and brine (150 ml), dried (MgSO$_4$) and evaporated to give the title compound as a brown oil (2.7 g, 85%).

$^1$H n.m.r. (CDCl$_3$): δ3.49 (m,2H,2×CH), 3.74 (m,2H,2× CH$_2$), 3.93 (m,2H,CH$_2$), 4.73 (s,2H,OCH$_2$O).

$^{13}$C n.m.r. (CDCl$_3$): δ64.3 (2×CH), 64.6 (2×CH$_2$) 94.3 (OCH$_2$O).

EI-MS:m/e 185 (MH$^+$), 157 (MH$^+$-N$_2$), 142 (M$^+$-N$_3$).

C$_5$H$_8$N$_6$O$_2$ requires: C: 32.61, H: 4.38, N: 45.63% found: C: 32.33, H: 4.67, N: 45.38%.

DESCRIPTION 13

(5R,6R)-Diamino-1,3-dioxepane

To a slurry of lithium aluminium hydride (2.1 g, 55.3 mmol) in dry tetrahydrofuran (70 ml) at 0° C. under an argon atmosphere was added dropwise a solution of (5R, 6R)-Diazido-1,3-dioxepane (2.6 g, 14.1 mmol) (D12) in dry tetrahydrofuran (50 ml). During the addition the reaction temperature was maintained below 10° C. with an ice-salt bath. One completion, the reaction mixture was allowed to warm to ambient temperature, and stirred for a further 1.5 hours. It was then recooled and the reaction quenched by addition of water (2 ml), 2M NaOH (2 ml), and water (4 ml), the temperature again being maintained below 10° C. by means of an ice-salt bath. The quenched reaction mixture was allowed to warm to ambient temperature, stirred for a further 2 hours, then filtered through Celite, and the filter pad washed well with tetrahydrofuran. The combined filtrates were evaporated to afford the title compound as a pale yellow oil (1 .3 g, 70%).

$^1$H n.m.r. (CDCl$_3$): δ1.56 (brs,4H,2×NH$_3$), 2.62 (m,2H, 2×CH), 3.58 (m,2H,CH$_2$), 3.77 (m,2H,2×CH$_2$), 4.72 (s,2H,OCH$_2$O)

$^{13}$C n.m.r. (CDCl$_3$): δ57.9 (2×CH), 67.5 (2×CH$_2$) 93.8 (OCH$_2$O).

C$_5$H$_{12}$N$_2$O$_2$ requires: C: 45.44, H: 9.15, N: 21.20% found: C: 45.13, H: 8.76, N: 1958%.

EI-MS:m/e 133 (MH$^+$), 116 (M$^+$-NH$_2$)$^+$, 90 (M-2NH$_2$)$^+$.

DESCRIPTION 14

Preparation of (5R,6R)-Di-(3,5-di-tert-butyl)salicylidenamino-1,3-dioxepane (5R,6R)-Diamino-1,3-dioxepane (1.0 g, 7.6 mmol) (D13) and 3,5-di-tert-butylsalicaldehyde (3.6 g, 15.4 mmol, 2 eq.) were dissolved in ethanol (100 ml), and the solution stirred under reflux for 3 hours. The reaction mixture was then allowed to cool, the solvent was evaporated, and the residue purified by column chromatography on silica, eluting with 4% diethyl ether in hexane. This afforded the title compound as a bright yellow foam (3.5 g, 82%).

$^1$H n.m.r. (CDCl$_3$): δ1.23 (s,18H,6×CH$_3$), 1.41 (s,18H,6× CH$_3$), 3.85 (m,2H,CH$_2$), 4.07 (m,2H,CH$_2$), 4.87 (s,2H, OCH$_2$O), 6.99 (d,2H,Ar), 7.33 (d,2H,Ar), 8.33 (s,2H, 2×CH=N), 13.20 (brs,2H,2×OH).

$^{13}$C n.m.r. (CDCl$_3$): δ29.4 (6×CH$_3$), 31.4 (6×CH$_3$) 34.1 (2×CCH$_3$), 35.0 (2×CCH$_3$), 67.7 (2×CH), 73.8 (2×CH$_2$) 94.2 (OCH$_2$O), 117.6, 126.4, 127.4, 136.6, 140.3, 157.9 (Ar), 168.4 (2×C=N)

C$_{35}$H$_{52}$N$_2$O$_4$ requires: C: 74.43, H: 9.28, N: 4.96% found: C: 74.56, H: 9.15, N: 4.92%

CI-MS:m/e 565 (MH$^+$).

DESCRIPTION 15

(3R,4R)-Diacetoxytetrahydropyran (D15)

A solution of 3,4-di-O-acetyl-D-Xylal (11.16 g) in 50% aqueous ethanol (400 ml) containing PtO$_2$ (400 mg) was hydrogenated at atmospheric pressure for 3.5 hours at 25° C. The suspension was filtered through celite, washed with 50% aqueous ethanol (50 ml) and water (50 ml), and the combined filtrate evaporated in vacuo to afford the title compound as a colourless oil, 9.6 g (85%).

δ(CDCl$_3$): 130–150 (1H,m), 2.10 (6H,S), 2.10–2.20 (1H, m), 3.35–3.60 (2H,m). 380–4.00 (2H,m), and 4.80–5.00 (2H,m).

2. Dictionary of Organic Compounds, 5th Edition, 1982, Chapman & Hall, London, 579 and references therein.

DESCRIPTION 16

(3R,4R)-Dimethanesultionyloxytetrahydropyran(D16)

Sodium (~50 mg) was dissolved in methanol (100 ml) at ambient. To the resulting solution was added a solution of the diester (D15) (9.56 g, 47.3 mmol) in methanol (100 ml) and the mixture stirred for 72 hours. Amberlite IR 120H$^+$ resin (20 g) was added and the mixture filtered. Concentration of the filtrate in vacuo afforded the diol as a colourless oil. This was dissolved in a mixture of tetrahydrofuran (220 ml) and diethyl ether (220 ml). Triethylamine (10.86 g, 107.5 mmol,) was added and the solution cooled to 0° C. Methanesulphonyl chloride (11.76 g, 102.7 mmol) was added dropwise at 0° C., the solution was stirred for a further hour then stored at 4° C. for 16 hours. The resulting suspension was filtered and the solids washed with tetrahydrofuran (2×95 ml) and diethyl ether (2×180 ml). The combined filtrate was evaporated in vacuo and the residue partitioned between ethyl acetate (200 ml) and 10% aqueous citric acid (200 ml). The organic phase was dried (MgSO$_4$), filtered and concentrated in vacuo to a colourless foam to afford the title compound, 12.07 g (93%).

δ(CDCl$_3$): 3.10 (6H,s), 2.00–2.40 (2H,m), 3.40–4.20 (4H, m), 4.55–4.65 (1H,m) and 4.70–4.85 (1H,m).

DESCRIPTION 17

(3R,4S)-Diaminotetrahydropyran (D17)

The dimesylate (D16) (12.07 g, 44 mmol) was dissolved in dimethylsulphoxide (88 ml) and treated with lithium azide (10.8 g, 220 mmol). The mixture was heated at 100° C. for 40 hours, then cooled to ambient and poured into water (1.03 L) and extracted with ethyl acetate (1.03 L, 2×0.59 L). The combined organic phase was washed with water (300 ml) and brine (300 ml), dried over MgSO$_4$ and concentrated in vacuo to give the crude diazide as a brown oil, 3.7 g. This was dissolved in tetrahydrofuran (45 ml), and added dropwise to a cold (0° C.) suspension of lithium aluminium hydride (3.34 g, 88 mmol) in tetrahydrofuran (220 ml), maintaining the temperature below +10° C. After completion of addition the suspension was stirred at 0° C. for 0.5 hours then warmed to ambient and stirred for 16 hours.

The mixture was recooled to 0° C. and quenched sequentially with water (3.34 ml) in tetrahydrofuran (5 ml), 15% aqueous sodium hydroxide (3.34 ml) and further water (10 ml). The mixture was allowed to warm to ambient, stirred for one hour then filtered through celite, rinsing with tetrahydrofuran (2×400 ml). The combined filtrate was concentrated in vacuo to give the title diamine (3) as a colourless oil, 2.62 g (51%).

δ(CDCl$_3$): 120–1.90 (6H,m), 2.40–2.50 (2H,m), 2.90–3.40 (2H,m) and 3.80–4.00 (2H,m).

DESCRIPTION 18

(3R,4S)-bis-(3,5-Di-tert-Butylsalicylideamino)tetrahydropyran, (D18)

To the diamine (D17) (2.55 g, 22 mmol) in ethanol (220 ml) was added 3,5-ditertbutylsalicaldehyde (10.3 g, 44 mmol). The mixture was heated at reflux for 2 hours, cooled to ambient filtered, and the crystalline product dried in vacuo to afford the title compound as yellow crystals, 4.81 g, (40%).

δ(CDCl$_3$): 1.20 (18H,s), 1.40 (18H,s), 1.50–2.20 (2H,m), 3.50–3.70 (4H,m), 4.00–4.15 (2H,m), 7.00 (2H,bs), 7.35 (2H,bs), 8.33 (1H,s), 8.37 (1H,s) and 13.20 (2H, bs).

DESCRIPTION 19

(3R,4S)-bis (3-tert-Butyl-5-methylsalicylideamino) tetrahydropyran (D19)

A solution of the diamine (D 17) (0.62 g, 5.35 mmol) and 3-tertbutyl-5-methylsalicaldehyde (2.05 g, 10.7 mmmol) in ethanol (40 ml) was heated at reflux for 2 hours. The solution was cooled then stored at 4° C. for 70 hours to afford a yellow precipitate. This was filtered, washed with cold 95% aqueous ethanol (5 ml) and dried in vacuo to afford the title compound, 1.22 g (49%).

δ(CDCl$_3$): 1.40 (18H,s), 1.80–2.20 (2H,m), 2.20 (6H,s), 3.40–3.70 (4H,m), 4.00–4.20 (2H,m), 6.80 (2H,bs), 7.05 (2H,bs), 8.27 (1H,s), 8.30 (1H,s) and 13.30 (2H, bs).

DESCRIPTION 20

(3S,4S)-bis (3,5-di-tert-Butylsalicylideamino) tetrahydrofuran (D20)

A solution of (S,S)-diamine (D6) (0.96 g, 9.4 mmol) and 3,5-di-tertbutylsalicaldehyde (4.4 g, 18.8 mmol) in ethanol (90 ml) was heated at reflux for 2 hours. The mixture was cooled to 0° C., filtered and the solids washed with cold ethanol and dried to afford the title compound as yellow crystals, 3.07 g (61%).

δ(CDCl$_3$): 1.27 (18H,s), 1.45 (18H,s), 3.95–4.10 (4H,m), 4.30–4.40 (2H,m), 7.05 (2H,d), 7.40 (2H,d), 8.35 (2H, s) and 13.20 (2H,s).

DESCRIPTION 21

(3S,4R)-Dihydroxy-(2R)-(hydroxymethyl)tetrahydropyran (D21)

A solution of D-Glucal (16.0 g, 0.11 mole) in 50% aqueous ethanol (500 ml) was treated with platinum oxide (0.75 g) and hydrogenated at ambient at atmospheric pressure for 5 hours. The suspension was treated with charcoal (50 g) filtered through celite (200 g) and the solids washed with 50% aqueous ethanol (300 ml). The combined filtered was evaporated in vacuo and dried over $P_2O_5$ to afford the title compound as a colourless oil, 16.0 g (99%).

δ($CD_3OD$): 1.50–1.70 (1H,m), 1.80–2.20 (1H,m), 3.00–3.20 (2H,m), 3.30–3.70 (3H,m), 3.80–4.00 (2H, m) and 4.90 (3H,bs)

3. Dictionary of Organic Compounds, 5th Edition, 1982, Chapman and Hall, London, 2754, and references therein.

DESCRIPTION 22

(3S,4R)-Dihydroxy-(2R)-(triphenyimethoxymethyl)tetrahydropyran (D22)

A solution of the triol (D21) (1.76 g, 11.9 mmol) in pyridine (20 ml) was treated with trityl chloride (3.31 g, 11.9 mmol) and 4-(dimethylamino)pyridine (50 mg). Diisopropylethylamine (1.92 g, 14.8 mmol, 1.25 eq) was added and the solution stirred for 4 hour at ambient temperature.

The mixture was poured into water (200 ml) and extracted with diethyl ether (2×200 ml). The combined organic phase was washed with 10% aqueous citric acid (100 ml) and brine (100 ml), dried over $MgSO_4$ and concentrated in vacuo to an oil. The residue was chromatographed on silica (eluent:gradient of methanol in chloroform) to afford the title compound as a colourless foam, 3.70 g (79.7%).

δ($CDCl_3$): 1.60–1.80 (1H,m), 1.90–2.00 (1H,m), 2.70 (2H,bs,$D_2O$ exch), 3.25–3.50 (5H,m), 3.60–3.70 (1H, m), 3.90–4.00 (1H,m) and 7.20–7.50 (15H,m).

DESCRIPTION 23

(3R,4R)-Dimethanesulphonyloxy-(2R)(triphenyimethoxymethyl)tetrahydropyran (D23)

To the diol (D22) (3.10 g, 7.95 mmol) in a mixture of diethyl ether and tetrahydrofuran (2:1,150 ml) was added triethylamine (1.76 g, 17.5 mmol). The mixture was cooled to 0° C. and methanesulphonyl chloride (1.91 g, 16.7 mmol) added. After 2 hours the suspension was filtered and the filtrate concentrated in vacuo, then redissolved in ethyl acetate (200 ml). The solution was washed with 10% aqueous citric acid (100 ml) and brine (50 ml), then dried over $MgSO_4$. Solvent was removed in vacuo and the residue dried to afford (12) as a colourless solid, 4.26 g (95%).

δ($CDCl_3$): 2.20–2.50 (2H,m), 2.50 (3H,s), 3.20–3.30 (1H, m), 3.40–3.60 (3H,m), 3.95–4.10 (1H,m), 4.70–4.80 (2H,m) and 7.20–7.50 (15H,m).

DESCRIPTION 24

(3S,4S)-bis(3,5-Di-tert-butylsalicylideamino)-(2R)-(triphenyl methoxymethyl)tetrahydropyran (D24)

A mixture of the dimesylate (D23) (2.85 g, 5.22 mmol) and lithium azide (1.28 g, 26.1 mmol) in dimethyl sulphoxide (20 ml) was heated at 100°–110° C. for 24 hour. The solution was cooled, poured into water (200 ml) and extracted with ethyl acetate (2×300ml). The combined organic phase was washed with water (2×300ml) and brine (300 ml), and dried over $MgSO_4$. Removal of the solvent afforded the intermediate diazide as a yellow foam (1.52 g).

A 1.40 g portion of the diazide in tetrahydrofuran (10 ml) was added to a suspension of lithium aluminium hydride (470 mg, 12.4 mmol) in tetrahydrofuran (30 ml) at 0° C. After stirring at 0° C. for 1 hour the mixture was allowed to warm to ambient and stirred for 16 hours. The suspension was recooled to 0° C. and quenched sequentially with water (0.5 ml), 15% aqueous sodium hydroxide (0.5 ml) and further water (1.5 ml). After warming the ambient and stirring for 1 hour the mixture was filtered, the solids washed with tetrahydrofuran (2×20 ml) and the combined filtrate evaporated to afford the crude diamine as a foam (1.28 g).

A portion of the diamine (1.18 g) and 3,5-di-tert butyl-salicaldehyde (1.42 g, 6.08 mmol) in ethanol (30 ml) was heated at reflux for 4 hour then cooled to ambient. Solvent was removed in vacuo and the residue chromatographed on silica (eluent: gradient of chloroform in hexane) to afford the title compound as a yellow powder, 210 mg, in 8.4% overall yield from (D23).

δ($CDCl_3$): 1.25 (9H,m), 1.30–1.60 (2H,m), 1.32 (9H,s) 1.40 (9H, s), 1.50 (9H,s), 2.40–2.55 (1H,s), 2.70–2.80 (1H,s), 3.30–3.60 (2H,m), 3.90–4.30 (1H,bs), 7.00–7.35 (16H,m), 7.38 (1H,bs), 7.45 (1H,bs), 8.30 (1H,s), 8.50 (1H 13.25 (1H,s) and 13.50 (1H,s).

DESCRIPTION 25

(±)trans-1-Benzoyl-3,4-bis(methanesulphonyloxy)piperidine (D25)

(±)trans-1-Benzoylpiperidine-3,4-diol (3 g, 13.6 mmol) was suspended in dichloromethane (70 ml) and triethylamine (5.74 ml, 43 mmol) was added. The mixture was cooled to −10° C. and methanesulphonyl chloride (2.6 ml, 34 mmol) added over 5 min. After a further 15 min the mixture was poured into ice-water (50 ml) and the organic layer washed with 5% aqueous citric acid (30 ml). The solution was dried over $MgSO_4$ and concentrated in vacuo to a foam, 5.3 g (100%).

$δ_H$ ($CDCl_3$):1.95 (2H,m), 2.30 (2H,m),3.15 (6H,s), 4.70 (2H,m), 4.85 (2H,m) and 7.45 (5H,m).

4. V. Petrow and O. Stepehnson, J Pharm. Pharmacol, 1962, 14, 306–314.

DESCRIPTION 26

(±)trans-1-Benzoyl-3,4-diazidopiperidine (D26)

A mixture of the dimesylate (D25) (5.3 g, 14 mmol) and lithium azide (3.4 g, 69 mmol) in dimethylsulphoxide (36 ml) was heated at 100° C. for 18 hours. After cooling the reaction mixture was partitioned between dichloromethane (200 ml) and water (50 ml). The aqueous phase was separated and further extracted with dichloromethane (100 ml, 50 ml) and the combined organic extracts washed with water (3×50 ml), dried ($Na_2SO_4$) and concentrated in vacuo. The residue was chromatographed on silica (eluent: gradient of methanol in dichloromethane) to afford the title compound as a colourless solid, 900 mg (24%).

$δ_H$ ($CDCl_3$): 1.60 (2H,m), 2.10 (2H,m),3.05 (2H,m), 3.20 (2H,m) and 7.40 (5H, m).

DESCRIPTION 27

(±)trans-1-Benzoyl-3,4-diaminopiperidine (D27)

A solution of the diazide (D26) (450 mg, 1.7 mmol) in ethanol (30 ml) was treated with Lindlar catalyst (5%Pd/CaCO$_3$, 250 mg) and stirred under hydrogen (1 atm) for 24 hour. The mixture was filtered and solvent removed in vacuo to afford the title compound as oil, 350 mg (94%).

$\delta$H (DMSO):1.20 (1H,m), 1.65–1.80 (2H,m),2.20 (2H,m), 2.70 (1H,m), 3.00 (1H,m), 3.30 (1H,m), 4.40 (1H,m) and 7.40 (5H,m).

DESCRIPTION 28

(−)trans-1-Benzoyl-3,4-bis(3,5-di-tert-butylsalicylideamino)piperidine (D28)

A solution of the amine (D27) (350 mg, 1.6 mmol) and 3,5-ditertbutylsalicaldehyde (960 mg, 4.1 mmol) in ethanol (40 ml) was heated at reflux for 3 hours. The mixture was cooled and filtered to afford the racemic bis-imine, 652 mg (63%).

A 100 mg sample was separated by chiral hplc (CHIRALPAK AD, eluent 2% ethanol in hexane) to afford the title compound as a single enantiomer, $[\alpha]^{25}$D=228° (c=0.13, CHCl$_3$).

$\delta$H (CDCl$_3$):1.20 (1 8H,s), 1.45 (1 8H,s), 2.00 (2H,m), 3.25 (2H,m), 3.45 (1H,m), 3.55 (1H,m), 4.35 (2H,m), 6.95 (2H,s), 7.40 (7H,m), 8.30 (2H,s) and 13.15 (2H, bs).

EXAMPLE 1

(±) 3,4-bis(3-tert-Butyl-5-methylsalicylideamino) tetrahydrofuran manganese (III) chloride (E1)

A suspension of the racemic ligand (D3) (690 mg, 1.53 mmol) in EtOH (25 ml) was heated with Mn(OAc)$_2$.4H$_2$O(750 mg, 3.06 mmol) at reflux for 18 h. LiCl (195 mg, 4.49 mmol) was added and reflux continued for a further 0.5 h. Solvent was removed in vacuo and the residue chromatographed on silica (Merck 9385, 100 g) eluting with a gradient of MeOH in CHCl$_3$, to afford the title compound as a brown powder (90 mg, 11% ) together with unreacted (D3), 420 mg (61% recovery).

EXAMPLE 2

The epoxidation of 2,2-dimethyl-6-pentafluoroethyl-2H-1-benzopyran using (E1) to give (±) 2,2-dimethyl-3,4-epoxy-6-pentafluoroethyl-2H- 1-benzopyran (E2)

Aqueous sodium hypochloride solution (16.75% w/v, 4.44 ml, 2 eq) was diluted to 12.5 ml with H20. 0.05M Na$_2$HPO$_4$ (aq) (5 ml) was added and th pH adjusted to 11.3. The resulting solution was cooled to 0° C. and added to a solution of 2,2-dimethyl-6-pentafluoroethyl-2H-1-benzopyran (1.39 g, 5 mmol) and the catalyst (E1) (45 mg, 0.1 mmol, 2 mol %) in CH$_2$Cl$_2$ (5 ml). The mixture was stirred at 0° C. for 1 h then allowed to warm to room temperature and stirred for a further 16 h.

Hexane (50 ml) and H$_2$O (25 ml) were added and the organic layer separated. The aqueous phase was washed with hexane (50 ml) and the combined organic phase dried over MgSO$_4$ and concentrated in vacuo to give a pale yellow oil, 1.42 g.

Quantitive hplc analysis showed this to contain 1.08 g (74%) of the desired epoxide (E2) together with a trace (<5% recovery) of starting material both compounds identical ($^1$H nmr) with authentic samples.

EXAMPLE 3

(S,S) trans 3,4-bis (3-tert Butyl-5-methylsalicylideamino)tetrahydrofuran manganese (III) chloride (E3)

Method A (using manganese (II) acetate)

A solution of (D7) (0.95 g, 2.11 mmol) and Mn(OAc)$_2$.4H$_2$O (1.03 g, 4.22 mmol) in EtOH (40 ml) was heated at reflux for 17 h. Lithium chloride (268 mg, 6.33 mmol) was added and reflux continued for a further 0.5 h. After cooling to ambient the solvent was removed in vacuo and the residue chromatographed on silica (Merck 9385, gradient of MeOH in CHCl$_3$) to afford (E3) as a brown powder, 26 mg (2.3%), together with unreacted (D7), 683 mg (72%).

Method B (using manganese (III) acetate)

A solution of (D7) (1.53 g, 3.4 mmol) in a mixture of CH$_2$Cl$_2$ (17 ml) and MeOH (17 ml) was treated with Mn(OAc)$_3$.2H$_2$O (0.01 g, 3.4 mmol). The mixture was heated at reflux for 3 h, cooled to ambient and treated with lithium chloride (0.21 g, 5.1 mmol). After stirring for 16 h the solvent was reduced in vacuo to ca. 8 ml, Et$_2$O (70 ml) was added and the suspension stirred for 1 h. The mixture was filtered and the solids washed with Et$_2$O (3×20 ml) and dried in vacuo to afford (E3) as a brown powder, 1.57 g (86%).

5 T. Matsushita and T. Shono, Bull. Chem. Soc. Japan, 1981, 54, 3743–3748.

EXAMPLE 4

The chiral epoxidation of 2,2-dimethyl-6-pentafluoroethyl-2H-1-benzopyran using (E3) to give (3R, 4R)-2,2-dimethyl-3,4-epoxy-6-pentafluoroethyl-2H-1-benzopyran (E4)

Aqueous sodium hypochlorite solution (16.75% w/v, 8.9 ml 20.0 mmol) was diluted to 25 ml with H$_2$O. 0.05M NaH$_2$PO$_4$ (aq) (10 ml) was added and the pH adjusted to 11.3. The resulting solution was cooled to 0° C. and added to a solution of 2,2-dimethyl-6-pentafluoroethyl-2H-1-benzopyran (2.78 g, 10.0 mmol) and the catalyst (E3) (0.108 g, 0.2 mmol, 2 mol%) in methylene chloride (10 ml). The mixture was stirred at 0° C. for 1 h then allowed to warm to room temperature and stirred for a further 20 h.

Hexane (100 ml) and H$_2$O (50 ml) were added and the organic layer separated. The aqueous phase was washed with hexane (100 ml) and the combined organic phase dried over MgSO$_4$ and concentrated in vacuo to give a pale yellow oil, 2.86 g.

Quantitative hplc analysis showed this to contain 2.09 g, (71% ) of the desired epoxide (E4) and a small quantity (about 10% ) of starting material, both compounds identical ($^1$H NMR, TLC, HPLC) with authentic samples, e.e.=66% by chiral HPLC.

EXAMPLE 5

Preparation of (R,R)-5,6-bis-(3,5-di-tert-butylsalicylidenamino)-1,3-dioxepane]-mangenese (III) chloride (5R,6R)-Di-(3,5-di-tert-butyl)salicylidenamino-1,3-dioxepane (1.0 g, 1.77 mmol) (D 14) and manganese (II) acetate tenhydrate (2.17 g, 8.87 mmol) were suspended in 95% ethanol (50 ml), and the mixture stirred under reflux overnight. Lithium chloride (0.38 g, 8.96 mmol) was then added and heating continued for a further 30 minutes. The reaction mixture was then cooled, water (60 ml) added, and filtered through Celite. The dark precipitate was washed well with water, then dissolved in dichloromethane (80 ml), dried (MgSO$_4$), and the solvent evaporated to give the title compound as a dark brown solid (0.9 g, 78%).

$C_{35}H_{50}N_2O_4MnCl$ requires: C:64.36, H:7.72, N:4.29%. found: C: 64.57, H: 7.57, N: 4.09% CI-MS: m/e 565 (MH-Mn,Cl)$^+$, 235 (3,5-di-tert-butylsalicaldehydeH)$^+$.

EXAMPLE 6

Preparation of (3S,4S)-2-2-dimethyl-3,4-epoxy-6-pentafluoroethyl-2H-1-benzopyran by oxidation of 2,2-dimethyl-6-pentafluoroethyl-2H- 1-benzopyran using sodium hypochlorite catalysed by (R,R)-5,6-bis-(3,5-di-tert-butylsalicylideamino)-1,3-dioxepane] -manganese (III) chloride Sodium hypochlorite solution (11.4% w/v, 13.1 ml, 2 eq.) was diluted to 25 ml with water, followed by the addition of 0.05 molar sodium dihydrogen phosphate (10 ml). The pH of this solution was adjusted to 11.3 with 2 molar aqueous sodium hydroxide, and it was then added to a solution of 2,2-dimethyl-6-pentafluoroethyl-2H- 1-benzopyran (2.78 g, 10 mmol), and (R,R)-[1,2-bis-(3,5-di-tert-butylsalicylidenamino) 1,3-dioxepane]-manganese (III) chloride (0.131 g, 2 mol %) in dichloromethane (10 ml), which had been cooled in an ice bath. The reaction mixture was allowed to warm to ambient temperature and stirred for 22 hours, by which time the reaction was essentially complete.

The reaction mixture was diluted with water (50 ml) and hexane (100 ml), filtered through Celite, the organic phase separated and the aqueous extracted with a further portion of hexane (100 ml). The combined organic phases were dried (MgSO$_4$) and evaporated to give the title compound as a yellowish solid (2.6 g, 88% ). Hplc determination of the chiral purity of the crude product gave an e.e. of 86.0%. The crude product was recrystallised from hexane to afford colourless crystals, m.p. 72°–73° C.

$^1$H n.m.r. (CDCl$_3$): δ1.29 (s,3H,CH$_3$), 159 (s,3H,CH$_3$), 3.53 (d,1H,H-3), 3.94 (d,1H,H-4), 6.90 (dd,1H,H-8), 7.46 (dd,1H,H-7), 7.57 (dd,1H,H-5)

$^{13}$C n.m.r. (CDCl$_3$): δ22.9 (CH$_3$), 25.5 (CH$_3$), 50.4 (C-3), 62.5 (C-4), 74.1 (C-2), 113.4 (tq,CF$_3$), 118.4 (C-8) 119.1 (qt,CF$_2$), 120.4 (C-4), 121.1 (t,C-6), 128.1, 128.6 (2×t,C-5,7), 155.7 (C-8').

EI-MS:m/e 294 M$^+$, 279 (M-CH3)$^+$.

$C_{13}H_{11}F_5O_2$ requires: C: 53.07, H: 3.77% found: C: 52.69, H: 3.82%.

EXAMPLE 7

(3R,4S)-bis-(3,5-di-tert-butylsalicylideamino)tetrahydropyran-manganese (III) chloride (E7)

A solution of the ligand (D 18) (4.81 g, 8.8 mmol) in dichloromethane-methanol (1:1, 88 ml) was treated with maganese triactate dihydrate (2.35 g, 8.8 mmol) and the mixture heated at reflux for 4 hours. Lithium chloride (0.56 g, 13.2 mmol) was added and heating at reflux continued for a further 1 hour. The mixture was cooled, concentrated in vacuo and the residue triturated with diethyl ether (220 ml). The solid product was filtered, washed with diethyl ether (2×65 ml) and dried to afford (5) as a brown powder, 5.3 g (94%).

EXAMPLE 8

The chiral epoxidation of 2,2-dimethyl-6-pentafluoroethyl-2H-1-benzopyran using (E7) to give (3S, 4S)-2,2-dimethyl-3,4-epoxy-6-pentafluoroethyl-2H-1-benzopyran (E8)

Aqueous sodium hypochlorite (15.24% w/v, 9.8 ml, 20 mmol) was diluted to 25 ml with H$_2$O. 0.05 M NaH$_2$PO$_4$(aq) (10 ml) was added and the pH adjusted to 11.3. The resulting solution was cooled to 0° C. and added to a solution of 2,2-dimethyl-6-pentafluoroethyl-2H-1-benzopyran (2.78 g, 10 mmol), and the catalyst (E7) (127 mg, 0.2 mol %) in dichloromethane (10 ml). The mixture was stirred at 0° C. for 1 hour then allowed to warm to ambient and stirred for a further 18 hours.

Hexane (100 ml) and water (50 ml) were added and the organic layer separated. The aqueous phase was washed with hexane (100 ml) and the combined organic phase dried over MgSO$_4$ and concentrated in vacuo to afford a yellow solid (2.60 g).

Quantitative hplc analysis showed this to contain 2.47 g (84%) of the desired epoxide (E8), identical ($^1$H nmr, tlc, hplc) with an authentic sample, ee=88.4% by chiral hplc.

EXAMPLE 9

(3R,4S )-bis-(3-tert-butyl-5-methylsalicylidenamino)tetrahydropyran-manganese (III) chloride (E9)

A solution of the ligand (D 19) (928 mg, 2 mmol) in dichloromethane-methanol (1:1, 20 ml) was treated with manganese triacetate dihydrate (536 mg, 2 mmol) and heated at reflux for 3 hours. The mixture was cooled to ambient, lithium chloride (128 mg, 3 mmol) was added and the solution stirred for 1 hour. The reaction mixture was concentrated in vacuo and the residue triturated with diethyl ether (40 ml). The solid product was filtered, washed with diethyl ether (2×15 ml) and dried in vacuo to afford the title compound as a brown powder, 1.09 g (98%).

EXAMPLE 10

The chiral epoxidation of 2,2-dimethyl-6-pentafluoroethyl-2H-1-benzopyran using (E9) to give (3S,4S )-2,2-dimethyl-3,4-epoxy-6-pentafluoroethyl-2H-1-benzopyran (E8)

Aqueous sodium hypochlorite (15.24% w/v, 9.8 ml, 20 mmol) was diluted to 25 ml with H$_2$O. 0.05 M NaH$_2$PO$_4$(aq) (10 ml) was added and the pH adjusted to 11.3. The resulting solution was cooled to 0° C. and added to a solution of 2,2-dimethyl-6-pentafluoroethyl-2H-1-benzopyran (2.78 g, 10 mmol) and the catalyst (E9) (111 mg, 0.2 mmol, 2 mol %) in dichloromethane (10 ml). The mixture was stirred at 0° C. for 1 hour then allowed to warm to ambient and stirred for a further 18 hour.

EXAMPLE 11

(3S,4S)-bis-(3,5-di-tert-Butylsalicylideamino)tetrahydrofuran-manganese (III) chloride (E11)

A solution of the ligand (D20) (1.07 g, 2 mmol) and manganese triacetate dihydrate (536 mg, 2 mmol) in a mixture of dichloromethane and methanol (1:1, 20 ml) was heated at reflux for 6.5 hour. The solution was cooled to ambient, lithium chloride (1 28 mg, 3 mmol) was added and the mixture stirred for 16 hours. The reaction mixture was concentrated in vacuo and the residue triturated with diethyl ether (50 ml). The solid product was filtered, washed with diethyl ether (2×15 ml) and dried in vacuo to afford the title compound as a brown powder, 1.12 g (89%).

EXAMPLE 12

The chiral epoxidation of 2,2-dimethyl-6-pentafluoroethyl-2H-1-benzopyran using (E11) to give (3R, 4R)-2,2-dimethyl-3,4-epoxy-6-pentafluoroethyl-2H-1-benzopyran (E4)

Aqueous sodium hypochlorite (15.24% w/v, 9.8 ml, 20 mmol) was diluted to 25 ml with $H_2O$. 0.05 M $NaH_2PO_4$(aq) (10 ml) was added and the pit adjusted to 11.3. The resulting solution was cooled to 0° C. and added to a solution of 2,2-dimethyl-6-pentafluoroethyl-2H-1-benzopyran (2.78 g, 10 mmol) and the catalyst (E11) (124.5 mg, 0.2 mmol, 2 mol %) in dichloromethane (10 ml). The mixture was stirred at 0° C. for 1 hour then allowed to warm to ambient and stirred overnight.

Hexane (100 ml) and water (50 ml) were added and the organic layer separated. The aqueous phase was washed with hexane (100 ml) and the combined organic phase dried over $MgSO_4$ and concentrated in vacuo to a yellow oil, 2.73 g.

Quantitative hplc analysis showed this to contain 2.47 g (84%) of the desired expoxide (E4), identical ($^1$H nmr, tlc, hplc) with an authentic sample, ee=85.6% by chiral hplc.

EXAMPLE 13

(3R,4S)-bis-(3,5-Di-tert-Butylsalicylidenamino)-(2R)-(triphenylmethoxymethyl) tetrahydropyran-manganese (III) chloride (E13)

To the ligand (D24) (160 mg, 195 μmol) in dichloromethane-methanol (3:2, 5 ml) was added NaOH (0.93 ml of 0.417 molar in methanol, 390 μmol) and manganese triacetate dihydrate (52.5 mg, 195 μmol). The solution was heated at reflux for 3 hours, lithium chloride (12.5 mg, 300 μmol) added and the mixture stirred for 15 hours.

Solvent was removed in vacuo and the residue triturated with diethyl ether (10 ml). The solid product was filtered, washed with diethyl ether (2×2 ml) and dried with afford the title compound as a brown powder, 136 mg (77%).

EXAMPLE 14

The chiral epoxidation of 2,2-dimethyl-6-pentafluoroethyl-2H-1-benzopyran using (E13) to give (3S, 4S)-2,2-dimethyl-3,4-epoxy-6-pentafluoroethyl-2H-1-benzopyran (E8)

Aqueous sodium hypochlorite (11.4% w/v, 2.6 ml, 4 mmol) was diluted to 5 ml with water. 0.05 M $NaH_2PO_4$(aq) was added and the pH adjusted to 11.3. The resulting solution was cooled to 0° C. and added to a solution of 2,2-dimethyl-6-pentafluoroethyl-2H-1-benzopyran (560 mg, 2 mmol) and the catalyst (E13) (36 mg, 0.04 mmol) in dichloromethane (2 ml) at 0° C. The reaction was stirred for 1 hour at 0° C. then at room temperature overnight.

Hexane (20 ml) and water (10 ml) were added and the organic layer separated. The aqueous phase was extracted with further hexane (20 ml) and the combined organic phase dried ($MgSO_4$) and the solvent removed in vacuo to afford (E8) as a yellow oil (0.55 g).

Quantitative hplc analysis showed this to contain 0.496 g (84%) of the desired epoxide (E8), identical ($^1$H nmr, tlc, hplc) with an authentic sample, ee=84% by chiral hplc.

EXAMPLE 15

(–)trans-1-Benzoyl-3,4-bis(3,5-di-tertbutylsalicylideamino) piperidine-manganese (III) chloride (E15)

A mixture of the (–) ligand (D28) (20 mg, 0.013 mmol) and manganese triacetate dihydrate (10 mg, 0.037 mmol) in dichloromethane-methanol (3:2, 5 ml) was heated at reflux for 4 hour. Lithium chloride (1.6 mg, 0.038 mmol) was added and reflux continued for a further 1 hour.

Solvent was removed in vacuo and the residue chromatographed on silica (eluent: 10% methanol in dichloromethane) to afford the title compound as a brown powder, 22 mg (97%).

EXAMPLE 16

The chiral epoxidation of 2,2-dimethyl-6-pentafluoroethyl-2H-1-benzopyran using (E15) to give (3R, 4R)-2,2-dimethyl-3,4-epoxy-6-pentafluoroethyl-2H-1-benzopyran (E4)

A solution of 2,2-dimethyl-6-pentafluoroethyl-2H-1-benzopyran (560 mg, 2 mmol) and the catalyst (E15) (22 mg, 0.03 mmol) in dichloromethane (2 ml) was cooled to 0° C. A mixture of aqueous sodium hypochlorite solution (2.6 ml of 11.4% w/v, 4 mmol) and 0.05 M $NaH_2PO_4$(aq) (2 ml, adjusted to pH 11.3) was added, the mixture stirred at 0° C. for 1 hour, then allowed to warm to ambient and stirred overnight.

The mixture was diluted with water (10 ml) and extracted with hexane (4×20 ml). The combined organic phase was washed with water (10 ml), dried over $Na_2SO_4$ and evaporated to afford the desired epoxide, 492 mg (83%). Analysis by chiral hplc showed an ee of 77%.

We claim:
1. A compound of formula (I):

Hexane (100 ml) and water (50 ml) were added and the organic layer separated. The aqueous phase was washed with hexane (100 ml) and the combined organic phase dried over $MgSO_4$ and concentrated in vacuo to give (E8) as a yellow oil (2.72 g, 93%), identical ($^1$H nmr, tlc, hplc) with an authentic sample, ee=73% by chiral hplc.

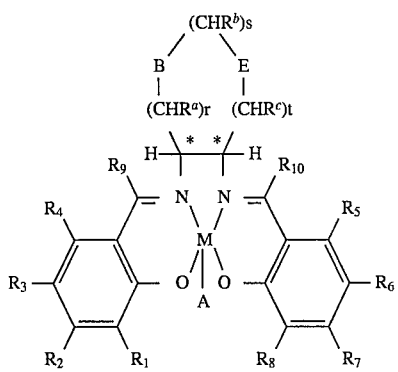

n which M is Mn;

A is a counter-ion if required;

r, s and t are independently 0 to 3 such that r+s+t is in the range of 1 to 3;

$R^a$, $R^b$, $R^c$ are each independently hydrogen or $CH_2OR'$ where R' is hydrogen or an organic group;

B and E are independently oxygen; $CH_2$, $NR^d$ in which $R^d$ is alkyl, hydrogen, alkylcarbonyl, or arylcarbonyl; or $SO_n$ where n is 0 or an integer 1 or 2; with the proviso that B and E are not simultaneously $CH_2$ and that when B is oxygen, $NR^d$ or $SO_n$, then r cannot be 0 and when E is oxygen, $NR^d$ or $SO_n$, then t cannot be 0;

$R_1$, $R_2$, $R_3$, $R_4$, $R_5$, $R_6$, $R_7$, $R_8$, $R_9$ and $R_{10}$ are independently hydrogen, alkyl or alkoxy.

2. A compound according to claim 1 in which Mn is in an oxidation state (II) or (III).

3. A compound according to claim 1 in which A is chlorine.

4. A compound according to claim 1 in which s and t are zero, r is 1 and $R^a$ is hydrogen, B is oxygen and E is $CH_2$; or r, s and t are 1, $R^a$, $R^b$ and $R^c$ are hydrogen and B and E are both oxygen; or s is zero, r and t are both 1, $R^a$ is hydrogen or triphenylmethyloxymethylene and $R^c$ is hydrogen, B is oxygen and E is —$CH_2$—; or r and t are both 1, s is zero, $R^a$ and $R^c$ are hydrogen, B is $NR^d$ where $R^d$ is phenyl carbonyl and E is $CH_2$.

5. A compound according to claims 1 in which $R_1$ and $R_8$ are tertiary butyl, $R_3$ and $R_6$ are tertiary butyl or methyl and $R_2$, $R_4$, $R_5$ and $R_7$ are hydrogen.

6. A compound according to claim 1 selected from the group consisting of (±) 3,4-bis (3-tert butyl-5-methylsalicylideamino)tetrahydrofuran manganese (III) chloride;

(S,S) trans 3,4-bis (3-tertbutyl-5-methylsalicylideamino)tetrahydrofuran manganese (III) chloride;

(R,R)-5,6-bis-(3,5-ditertbutylsalicylidenamino)-1,3-dioxepane]-mangenese (III) chloride;

(3R,4S)-bis-(3,5-ditertbutylsalicylideamino)tetrahydropyran-manganese (IH) chloride;

(3R,4S)-bis-(3-tertbutyl-5-methylsalicylidenamino)tetrahydropyran-man ganese (III) chloride;

(3S,4S)-bis-(3,5-ditertbutylsalicylideamino)tetrahydrofuran-manganese (IH) chloride;

(3R,4S)-bis-(3,5-ditertbutylsalicylidenamino)-(2R)-(triphenylmethoxymethyl)tetrahydropyran-manganese (III) chloride; and (−)trans-1-benzoyl-3,4-bis(3,5-di-tertbutylsalicylideamino) piperidine-manganese (III) chloride.

7. A process for enantioselectively epoxidising a prochiral olefin in the presence of an oxygen source and a chiral catalyst of formula (I) as defined in claim 1.

8. A process according to claim 7 in which the prochiral olefin comprises one of the following list of groups as pan of its structure: cyclohexene, 5,6-dihydro-2H-pyran, 1,2,5, 6-tetrahydropyridine, 1,2,3,4-tetrahydropyridine and 5,6-dihydro-2H-thiopyran.

9. A process according to claim 8 in which the prochiral olefin comprises one of the following list of groups as pan of its structure: 1,2-dihydronaphthalene, 2H-chromene, 1,2-dihydroquinoline, 1,2-dihydroisoquinoline and 2H-thiochromene.

10. A process according to any one of claim 9 in which the prochiral olefin is 2,2-dimethyl-6-pentafluoroethyl-2H-1-benzopyran.

11. A process according to claim 10 in which the 2,2-dimethyl-6-pentafluoroethyl-chromene(3S,4S)-epoxide product is subsequently converted to trans-6-pentafluoroethyl-3,4-dihydro-2,2-dimethyl-4R (piperidine-2-on-1-yl)-2H-1-benzopyran-3S-ol.

* * * * *